United States Patent [19]

Suh et al.

[11] Patent Number: 4,683,306
[45] Date of Patent: Jul. 28, 1987

[54] PROCESS FOR THE PREPARATION OF 3,4-DIHYDRO-2-SUBSTITUTED-2H-1,2-THIAZINE-CARBOXYLIC ACID 1,1-DIOXIDE DERIVATIVES

[75] Inventors: Jung J. Suh; You H. Hong, both of Seoul, Rep. of Korea

[73] Assignee: YuHan Corporation Co., Ltd., Seoul, Rep. of Korea

[21] Appl. No.: 630,393

[22] Filed: Jul. 13, 1984

[51] Int. Cl.$^4$ .................. C07D 279/02; C07D 513/04
[52] U.S. Cl. ........................................ 544/33; 544/48; 544/49
[58] Field of Search ......................... 544/49, 33, 48

[56] References Cited

U.S. PATENT DOCUMENTS

| | | | |
|---|---|---|---|
| 3,501,466 | 3/1970 | Rasmussen | 544/49 |
| 3,892,740 | 7/1975 | Lombardino | 544/49 |
| 3,898,218 | 8/1975 | Kaminsky | 544/33 |
| 3,900,470 | 8/1975 | Rasmussen | 544/49 |
| 3,992,535 | 11/1976 | Trummlitz et al. | 544/33 |
| 4,137,313 | 1/1979 | Trummlitz et al. | 544/33 |
| 4,259,336 | 3/1981 | Engel et al. | 544/33 |
| 4,309,427 | 1/1982 | Lombardino | 544/49 |
| 4,478,996 | 10/1984 | Almenara | 544/49 |

*Primary Examiner*—John M. Ford
*Attorney, Agent, or Firm*—Birch, Stewart, Kolasch & Birch

[57] ABSTRACT

Process for the preparation of 3,4-dihydro-2-substituted-4(or 3)-oxo-2H-1,2-thiazine-3(or 4)-carboxylic acid 1,1-dioxide magnesium chelate derivatives and its acids by reacting appropriately 3,4-dihydro-2-substituted-4(or 3)-oxo-2H-1,2-thiazine 1,1-dixoides with alkylmagnesiumcarbonate and then hydrolyzing and its use as intermediates for the preparation of N-substituted-2-substituted-2H-1,2-thiazine-3(or 4)-carboxamide-1,1-dioxide derivatives, effective antiinflammatory agents.

4 Claims, No Drawings

PROCESS FOR THE PREPARATION OF 3,4-DIHYDRO-2-SUBSTITUTED-2H-1,2-THIAZINE-CARBOXYLIC ACID 1,1-DIOXIDE DERIVATIVES

BACKGROUND OF THE INVENTION

1. Field of the Invention

This invention relates to a process for the preparation of 3,4-dihydro-2-substituted-4(or 3)-oxo-2H-1,2-thiazine-3(or 4)-carboxylic acid 1,1-dioxide derivatives, valuable intermediates for the preparation of non-steroidal antiinflammatory agents.

More particularly, it relates to the preparation of the aforementioned carboxylic acid magnesium chelate derivatives and its acid by reacting appropriately 3,4-dihydro-2-substituted-4(or 3)-oxo-2H-1,2-thiazine 1,1-oxide compounds with alkylmagnesium carbonates and then hydrolysing the obtained magnesium chelates in the presence of acids respectively and to the their as intermediates for the preparation of N-substituted-4(or 3)-hydroxy-2-substituted-2H-1,2-thiazine-3(or 4-carboxamide 1,1-dioxide derivatives.

2. Description of the Prior Art

The instability of $\beta$-keto carboxylic acid represented by the general formula (I) or (II), evidenced by their tendency to undergo decarboxylation and therefore to form a cause of lower yield of the object compound resulting therefrom is well known to those skilled in the art. That is, U.S. Pat. No. 3,892,740, issued on July 1, 1975, described that 3,4-dihydro-4-oxo-2H-1,2-benzothiazine-3-carboxylic acid, 1,1-dioxides have been prepared by hydrolysis of the corresponding ester but decarboxylated rapidly. The observed instability arises from their $\beta$-keto structure.

U.S. Pat. No. 4,100,347, issued on July 11, 1978 discloses that the decarboxylation can be avoided by hydrolysis, in the presence of hydroxide ions, of an alkyl ester or aralkyl ester of 3,4-dihydro-2-methyl-4-oxo-2H-1,2-benzothiazine-3-carboxylic acid 1,1-dioxide to form the corresponding 3,4-dihydro-2-methyl-4-oxo-2H-1,2-benzothiazine-3-carboxylic acid 1,1-dioxide.

SUMMARY OF THE INVENTION

It has been unexpectedly and surprisingly found that when a 3,4-dihydro-2-substituted-4-oxo-2H-1,2-thiazine 1,1-dioxide of the formula (III)

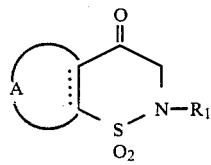
(III)

wherein A together with the two carbon atoms to which it is attached forms the group

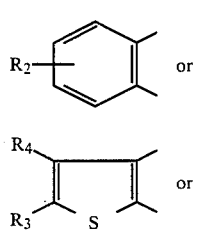
(a)

(b)

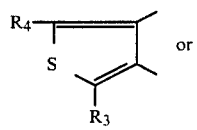
(c)

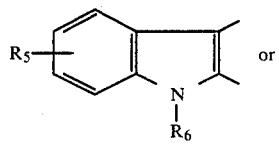
(d)

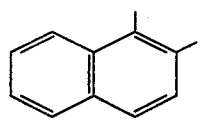
(e)

and the broken line represents the double bond in (a), (b), (d), (e); $R_1$ is lower alkyl having from one to 3 carbon atoms; $R_2$ is hydrogen, halogen, nitro, trifluoromethyl, lower alkyl having from one to 5 carbon atoms, lower alkoxy having from one to 3 carbon atoms in the alkyl moiety, phenyl, phenyl lower alkyl having from one to 3 carbon atoms in the alkyl moiety; $R_3$ and $R_4$ each is a hydrogen atom or a lower alkyl group; $R_5$ is hydrogen, fluorine, chlorine, bromine, methoxy, methyl, ethyl or trifluoromethyl; $R_6$ is methyl or ethyl or a. 3,4-dihydro-2-substituted-3-oxo-2H-thiazine 1,1-dioxide of the formula (IV)

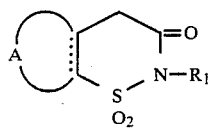
(IV)

wherein A and $R_1$ are as defined above, is reacted with alkylmagnesium carbonates of the formula (VII)

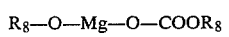

$R_8-O-Mg-O-COOR_8$ (VII)

wherein $R_8$ is lower alkyl having from one to 3 carbon atoms, to form new intermediates of the formulae (VIII) and (IX)

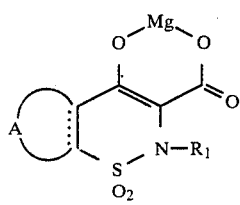
(VIII)

and

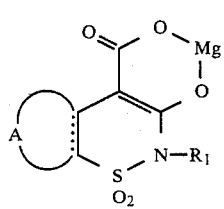
(IX)

wherein A and $R_1$ are as defined above, and then, the obtained magnesium chelates are hydrolysed in the presence of acids to form the formulae (I) and (II)

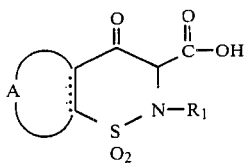 (I)

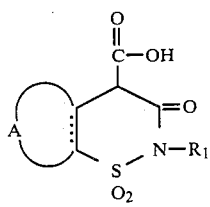 (II)

wherein A and $R_1$ are as defined above, in high yield and high purity.

The magnesium chelates and the corresponding acids obtained are valuable intermediates in synthesizing non-steroidal antiinflammatory agents such as those compounds having the formulae (V) and (VI)

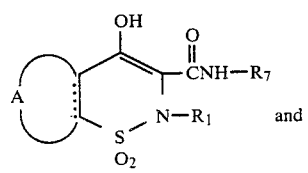 (V)

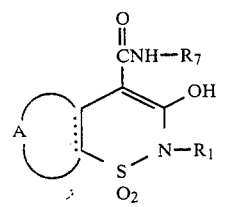 (VI)

wherein A and $R_1$ are as defined above; $R_7$ is hydrogen, lower alkyl having from one to 3 carbon atoms or a phenyl group which may be substituted by halogen, hydroxyl, lower alkyl, trifluoromethyl or lower alkoxy or phenyl lower alkyl having from one to 3 carbon atoms in the alkyl moiety or the residue of an aromatic heterocyclic ring containing from 1 to 4 hetero atoms, which may be substituted by one or two lower alkyl groups.

DETAILED DESCRIPTION OF THE INVENTION

This invention relates to a process for the preparation of 3,4-dihydro-2-substituted-4(or 3)-oxo-2H-1,2-thiazine-3(or 4)-carboxylic acid 1,1-dioxide magnesium chelate derivatives and corresponding acids of the formula (VIII), (IX) and (I), (II)

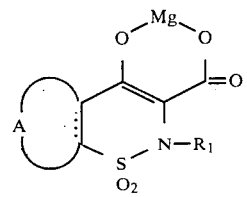 (VIII)

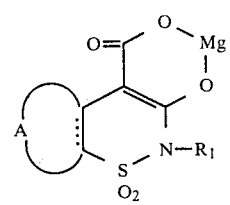 (IX)

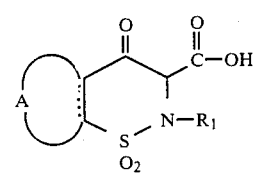 (I)

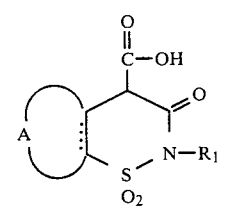 (II)

wherein A together with the two carbon atoms to which it is attached forms the group

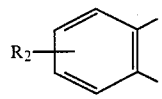 (a)

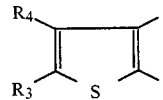 (b)

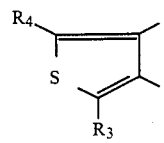 (c)

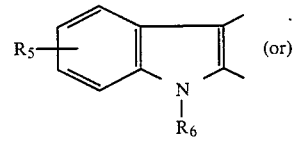 (d)

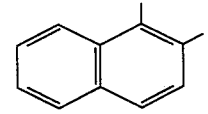 (e)

and the broken line represents the double bond in (a), (b), (d), (e); $R_1$ is lower alkyl having from one to 3 carbon atoms; $R_2$ is hydrogen, halogen, nitro, trifluoromethyl, lower alkyl having from one to 5 carbon atoms, lower alkoxy having from one to 3 carbon atoms in the alkyl moiety, phenyl or phenyl lower alkyl having from one to 3 carbon atoms in the alkyl moiety; $R_3$ and $R_4$ each is a hydrogen atom or a lower alkyl group; $R_5$ is hydrogen, fluorine, chlorine, bromine, methoxy, methyl, ethyl or trifluoro methyl; $R_6$ is methyl or ethyl and to their use as intermediates for the preparation of N-substituted-2-substituted-2H-1,2-thiazine-3(or 4)-carboxamide 1,1-dioxide derivatives of the formulae (V) and (VI), which are effective antiinflammatory agents,

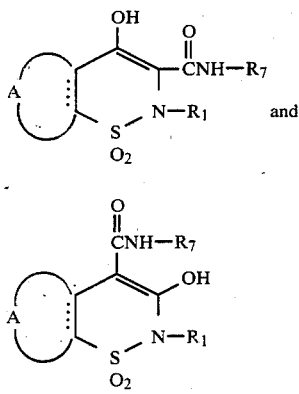

wherein A and $R_1$ are as defined above; $R_7$ is hydrogen, lower alkyl having from one to 3 carbon atoms, lower alkoxy having from one to 3 carbon atoms in the alkyl moiety, or a phenyl group which may be substituted by halogen, hydroxyl; lower alkyl, trifluoro methyl or lower alkoxy or phenyl lower alkyl having from one to 3 carbon atoms in the alkyl moiety, or a phenyl group which may be substituted by halogen, hydroxyl lower alkyl, trifluoromethyl or lower alkoxy or phenyl lower alkyl having from one to 3 carbon atoms in the alkyl moiety, or the residue of an aromatic heterocyclic ring containing from 1 to 4 hetero atoms, which may be substituted by one or two lower alkyl groups.

Accordingly, one object of this invention is to provide a new process for the preparation of 3,4-dihydro-2-substituted-4(or 3)-oxo-2H-1,2-thiazine-3(or 4)-carboxylic acid 1,1-dioxide magnesium chelate derivatives and the corresponding acids.

A further object of this invention is to use the obtained acid magnesium chelate compounds and the corresponding acids for the preparation of N-substituted-4(or 3)-hydroxy-2-substituted-2H-1,2-thiazine-3(or 4)-carboxamide 1,1-dioxide derivatives. The processes described in the said prior art use, as starting material, alkyl 3,4-dihydro-2-methyl-4-oxo-2H-1,2-benzothiazine-3-carboxylate 1,1-dioxides and hydrolyse in alkaline condition to obtain the objective compounds in low yield as follows:

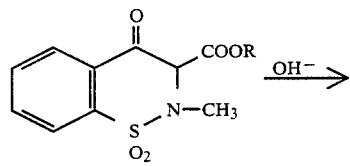

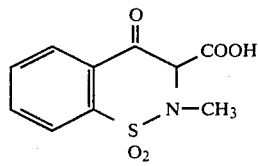

wherein R is lower alkyl.

But, in contrast thereto, this invention uses, as starting material, 3,4-dihydro-2-substituted-4(or 3)-oxo-2H-1,2-thiazine 1,1-dioxides of the formulae (III) and (IV)

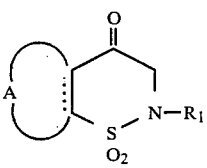

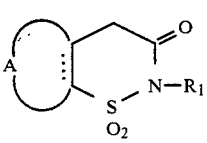

wherein A and $R_1$ are as defined above, and obtains the said compounds of the formulae (VIII), (IX), (I) and (II) quantitatively with simple procedures.

The object compounds (VIII), (IX), (I) and (II) can be prepared by the following equations:

Process 1

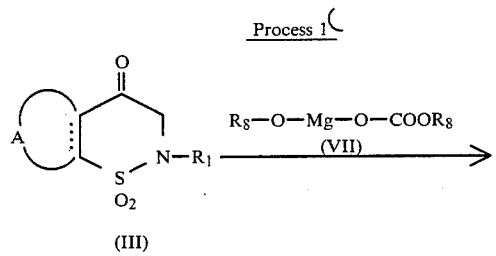

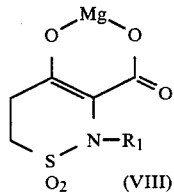

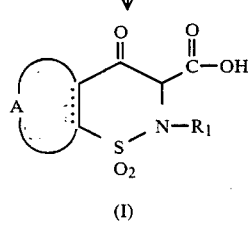

Process 2

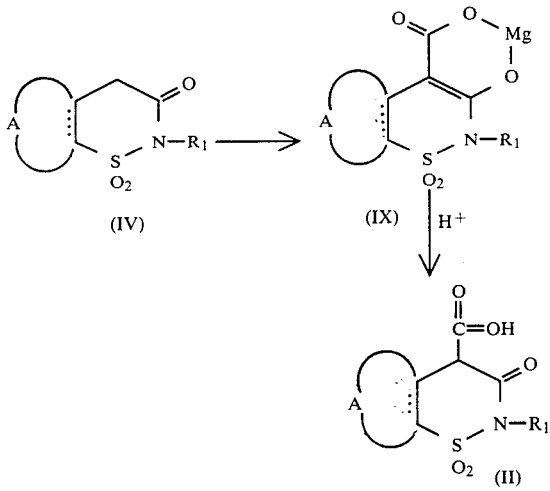

wherein A, $R_1$, $R_8$ are as defined above.

Suitable examples of alkyl represented by $R_1$, $R_8$ are methyl or ethyl.

The most preferred ones among the the formula (VIII), (IX), (I) and (II) are the ones in which $R_2$ is methyl.

These reactions are usually carried out in a conventional organic solvent such as N,N-dimethylformamide, dimethylsulfoxide or the like which does not adversely influence the reaction.

The reaction temperature is not critical and the reaction is usually carried out under warming or heating. The preferred temperature is from 50° C. to 150° C. It is preferred that the reaction is carried out at about melting temperature of the compounds of the formula (III) or (IV).

The reaction of the compounds of the formula (III) or (IV) with the compound of the formula (VII) is usually completed within 1-5 hours.

The compounds of the formula (VII), the reactant, are usually used in the amounts of 1-10 equivalents. The preferable amounts of the compounds of the formula (VII) are 4-7 equivalents. Firstly, the compound of the formula (III) or (IV) and the compound of the formula (VII) are suspended in the said unreactive solvent. After the reaction is completed, the reaction mixture is poured into chilled water.

By pouring the reaction mixture of the first step in the process 1 or 2 into chilled water, the mixture compound of the formula (VIII) or (IX) and magnesium hydroxide is obtained.

Secondly by pouring the reaction mixture of the first step in the process 1 or 2 into chilled hydrochloric acid, the compound of the formula (I) or (II) is obtained.

It is preferable that the neutralization procedure is carried out, in contact with an appropriate organic solvent.

Aprotic solvents such as hexane, ethers such as dimethyl ether or diethyl ether, ethyl acetate, dichloromethane or the like are suitable for such purpose.

It is preferable that neutralization is carried out by adding ice chips and after separating the organic layer, the organic solvent is evaporated in vacuo to obtain the compound of the formula (I) or (II) in a pure state nearly quantitatively.

The obtained compound of the formula (VIII), (IX), (I) or (II) is used as an intermediate for the preparation of the said N-substituted-4(or 3)-hydroxy-2-substituted-2H-1,2-thiazine-3(or 4)-carboxamide 1,1-dioxide derivatives, which are effective antiinflammatory agents.

According to the prior art, the yield of the object compound is very low.

This invention uses a mixed anhydride method in order to avoid decarboxylation and by acylating of the intermediate compound (VIII), (IX), (I) or (II) with at least 2 molar amount of the acylating agent, the keto group in the position 4(or 3) of the compound (I) (or (II)) is protected and at the same time by adding and reacting an appropriate amine ($R_7$—$NH_2$), amidation reaction arises.

The obtained compound is hydrolysed in the presence of alkali and then is neutralized with mineral acid such as hydrochloric acid, sulfuric acid, or the like to obtain the compound of the formula (V) or (VI).

The reaction equations are as follows:

Process 3

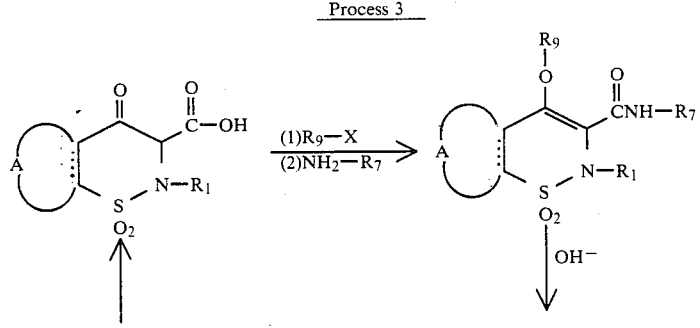

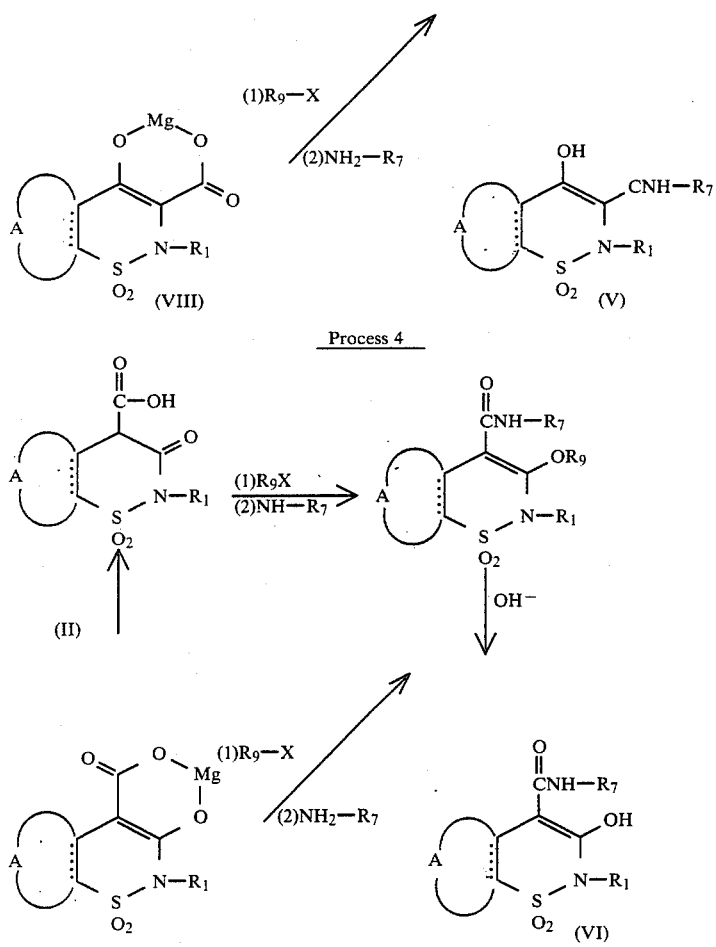

Wherein A, $R_1$ and $R_7$ are as defined above and $R_9$ is trialkylacetyl having from one to 3 carbon atoms in the alkyl moiety, benzenesulfonyl or substituted benzenesulfonyl and X is halogen.

Suitable examples of $R_9$ are trimethylacetyl, benzenesulfonyl, p-toluenesulfonyl.

The said compounds of the formulae (I), (II), (V) and (VI) exist as mixtures of keto and enol tautomers. It is evident that both tautomers of the said compounds described herein are embraced within the scope of this invention.

For convenience, only one of the tautomers is illustrated.

The process for the preparation of the compound of the formula (III) or (IV) is disclosed in the prior art (J. Org. Chem., 31, 162, 1966 and J. Med. Chem., 14, 973, 1971).

The following examples are given only for the purpose of illustrating this invention in more detail.

EXAMPLE 1

Preparation of 3,4-dihydro-2-methyl-4-oxo-2H-1,2-benzothiazine-3-carboxylic acid 1,1-dioxide To 6.34 g (0.03 mole) 3,4-dihydro-2-methyl-4-oxo-1,2-benzothiazine 1,1-dioxide, 19.5 g (0.15 mole) methylmagnesiumcarbonate in 150 ml N,N-dimethyl formamide were added. The mixture was stirred at 140°–150° C. for 2 hours. The resulting solution was poured quickly into a mixture of 200 ml conc-hydrochloric acid, 200 g ice chips and 500 ml diethyl ether. After stirring the mixture for 10 minutes, the diethylether layer was separated and the separated diethyl ether solution was evaporated in vacuo. The precipitated pale yellow crystals were filtered and recrystallized in dilute methanol solution to obtain 7.21 g of the title compound as white crystals. Yield: 94%

EXAMPLE 2

Preparation of N-(2-pyridyl)-4-(benzenesulfonyl)-2-methyl-2H-1,2-benzothiazine-3-carboxamide 1,1-dioxide 1.29 g (0.005 mole) 3,4-dihydro-2-methyl-4-oxo-2H-1,2-benzothiazine-3-carboxylic acid 1,1-dioxide and 4.18 ml triethylamine were dissolved in 15 ml tetrahydrofuran and the mixture cooled to −5° C. and 1.91 ml benzenesulfonyl chloride was added slowly to the stirred mixture and stirred, and after one hour 0.52 g 2-aminopyridine was added to the mixture. The temperature of the mixture was raised slowly to ambient temperature and stirred for 4 hours, and twice the volume of ice water was added to the mixture to form precipitates. The obtained precipitates were filtered and recrystallized in ethanol and ethylether to obtain 1.6 g of the title compound. Yield: 68%. m.p 192°–195° C.

EXAMPLE 3

Preparation of
N-(2-pyridyl)-4-(4'-toluenesulfonyl)-2-methyl-2H-1,2-benzothiazine-3-carboxamide 1,1-dioxide 1.68 g of the title compound was obtained in the substantially same manner as that of Example 2 from 1.2 g (0.005 mol) 3,4-dihydro-2-methyl-4-oxo-2H-1,2-benzothiazine-3-carboxylic acid 1,1-dioxide and 4.18 ml triethylamine, 0.52 g 2-aminopyridine and 2.86 g p-toluenesulfonyl chloride instead of benzenesulfonyl chloride.

Yield: 69% m.p. 190°–194° C.

EXAMPLE 4

Preparation of
N-(2-pyridyl)-4-hydroxy-2-methyl-2H-1,2-benzothiazine-3-carboxamide 1,1-dioxide 2.36 g (0.005 mole) N-(2-pyridyl)-4-(benzenesulfonyl)-2-methyl-2H-1,2-benzothiazine-3-carboxamide 1,1-dioxide was dissolved in 50 ml water containing 1.0 g sodium hydroxide. After it was completely hydrolysed, the solution was neutralized with conc-hydrochloric acid to form precipitates. The obtained precipitates were filtered and recrystalized with methanol and N,N-dimethyl formamide and n-hexane to obtain 1.51 g of the title compound. Yield: 91%. m.p. 198°–201° C.

EXAMPLE 5

Preparation of
N-(2-thiazolyl)-4-hydroxy-2-methyl-2H-1,2-benzothiazine-3-carboxamide 1,1-dioxide 1.48 g of the title compound was obtained in substantially the same manner as that of Example 4 from 1.9 g (0.005 mol) N-(2-thiazolyl)-4-benzenesulfonyl)-2-methyl-2H-1,2-benzothiazine-3-carboxamide 1,1-dioxide. Yield: 88%. m.p. 250°–252° C.

EXAMPLE 6

Preparation of
N-(5-methyl-3-isoxazolyl)-4-hydroxy-2-methyl-2H-1,2-benzthiazine-3-carboxamide 1,1-dioxide 1.41 g of the title compound was obtained in the substantially same manner as that of Example 4 from 1.96 g (0.005 mol) N-(5-methyl-3-isoxazolyl)-4-(benzensulfonyl)-2-methyl-2H-1,2-benzothiazine-3-carboxamide 1,1-dioxide. Yield 89%. m.p. 254°–256° C.

EXAMPLE 7

Preparation of the mixture of
3,4-dihydro-2-methyl-4-oxo-2H-1,2-benzothiazine-3-carboxylic acid 1,1-dioxide magnesium chelate and magnesium hydroxide To 6.34 g (0.03 mole) 3,4-dihydro-2-methyl-4-oxo-2H-1,2-benzothiazine 1,1-dioxide were added 2M-magnesiummethylcarbonate N,N-dimmethylform amidesolution 150 ml (0.3 mole). The mixture was stirred at 140°–150° C. for 2 hours. The resulting solution was poured slowly into 500 ml chilled water. After stirring the mixture for 1 hour, it and was filtered to obtain 23.6 g of the title mixture. Yield 98%.

EXAMPLE 8

Preparation of
N-(2-pyridyl)-4-(benzensulfonyl)-2-methyl-2H-1,2-benzothiazine-3-carboxamide 1,1-dioxide 4.01 g (0.005 mole) of the mixture of 3,4-dihydro-2-methyl-4-oxo-2H-1,2-benzothiazine-3-carboxylic acid 1,1-dioxide magnesium chelate and magnesium hydroxide were added to 15 ml tetrahydrofurane and the mixture cooled to −5° C. and 12.76 ml benzensulfonyl chloride was added slowly to the stirred mixture. After stirring the mixture for one hour, to the mixture 0.52 g 2-aminopyridine was added. The temperature of the mixture was raised slowly to ambient temperature and stirred for four hours.

Twice the volume of ice water was added to the mixture to form precipitates. The obtained precipitates were filtered and recrystallized from ethanol and ethylester to obtain 0.85 g of the title compound. Yield 36%. m.p 191°–193° C.

EXAMPLE 9

Preparation of
3-hydroxy-2-methyl-2H-1,2-benzothiazine-4-carboxanilide 1,1-dioxide In a four neck flask equipped with reflux condenser, stirrer, thermometer and calcium drying tube, 1.06 g (0.005 mole) 3,4-dihydro-2-methyl-3-oxo-2H-1,2-benzothiazine 1,1-dioxide and 2.6 g (0.02 mole) methylmagnesiumcarbonate in 20 ml N,N-dimethylformamide were added. The mixture was stirred at 90°–100° C. for 3 hours. The resulting solution was poured quickly into a mixture of 30 ml conc-hydrochloric acid, 70 g ice chips and 200 ml diethylether. After stirring the mixture for 10 minutes, the separated diethylether layer was evaporated in vacuo to obtain 1.25 g of 3,4-dihydro-2-methyl-3-oxo-2H-1,2-benzothiazine-4-carboxylic acid 1,1-dioxide. The obtained compound was dissolved in 20 ml benzene and to the solution, 1.3 ml thionyl chloride and 0.4 ml N,N-dimethylformamide were added.

The mixture were stirred in a water bath for 3 hours and the resulting pale yellow precipitates were separated by filtration and washed with small amount of benzene. The precipitates were dissolved in 10 ml N,N-dimethylformamide and 1.02 g aniline was added thereto. The mixture was stirred at ambient temperature for 3 hours. To the resulting mixture, twice the volume of ice water was added to form precipitates. The obtained precipitates were filtered and recrystallized to obtain 0.85 g of the title compound. Yield: 51.2%. m.p 155°–156° C.

What we claim are:

1. A process for the preparation of a partially hydrolyzed compound of formula (V) or (VI), respectively:

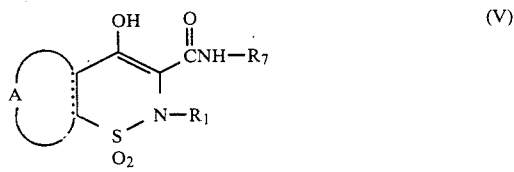

-continued

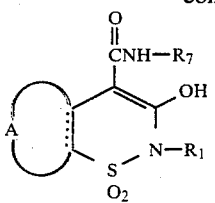
(VI)

which comprises reacting a compound of the formula I or II:

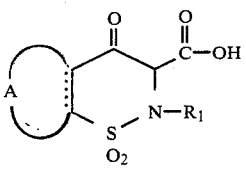
(I)

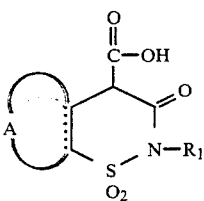
(II)

with at least a 2 molar amount of the acylating agent $R_9$—X and with $R_7$—$NH_2$ wherein A together with the two carbon atoms to which it is attached forms one of the groups (a)-(e):

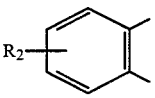
(a)

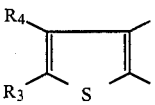
(b)

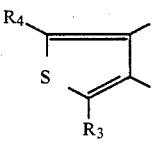
(c)

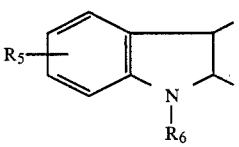
(d)

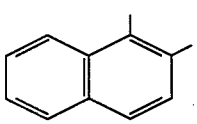
(e)

and the broken line represents the double bond in (a), (b), (d) and (e); $R_1$ is lower alkyl having from 1 to 3 carbon atoms; $R_2$ is hydrogen, halogen, nitro, trifluoromethyl, lower alkyl having from 1 to 5 carbon atoms, lower alkoxy have from 1 to 5 carbon atoms in the alkyl moiety, phenyl, or phenyl lower alkyl having from 1 to 3 carbon atoms in the alkyl moiety; $R_3$ and $R_4$ each is a hydrogen atom or a lower alkyl group; $R_5$ is hydrogen, fluorine, chlorine, bromine, methoxy, methyl, ethyl or trifluoromethyl; and $R_6$ is methyl or ethyl; $R_7$ is hydrogen, lower alkyl having from 1 to 3 carbon atoms, lower alkoxy having from 1 to 3 carbon atoms in the alkyl moiety thereof, phenyl which may be substituted by halogen, hydroxyl, lower alkyl trifluoromethyl, or lower alkoxy or phenylalkyl having from 1 to 3 arbon atoms in the alkyl moiety; and $R_9$ is trialkylacetyl having from 1 to 3 carbon atoms in the alkyl moiety, benzenesulfonyl or substituted benzenesulfonyl in which the substituent is methyl, and X is halogen, to form an N-substituted-4(or 3)-substituted-2-substituted 2H-1,2-thiazine-3(or 4)carboxamide 1,1-dioxide derivative of the formula (X) or (XI):

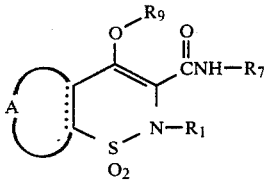
(X)

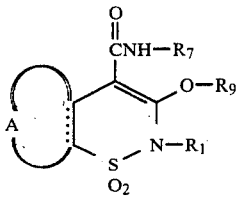
(XI)

wherein the reaction temperature range is from $-5°$ C. to ambient temperature, the total reaction time is 5 hours and in which $R_9$—X and $R_7NH_2$ are simultaneously present, and further comprises partially hydrolyzing a compound of said formula (X) or (XI) in the presence of alkali and neutralizing the resulting compound with a mineral acid to give a compound of formula (V) or (VI), respectively:

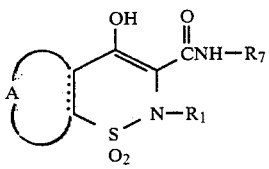
(V)

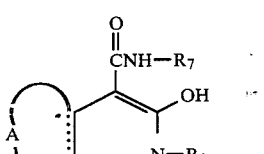
(VI)

2. A process according to claim 1, wherein the trialkylacetyl is trimethylacetyl.

3. A process according to claim 1, wherein $R_9$ is benzenesulfonyl.

4. A process according to claim 1, wherein $R_9$ is substituted benzenesulfonyl in which the substituent is methyl.

* * * * *